April 27, 1965 G. Y. KAWACHI Plant Pat. 2,501
POINSETTIA PLANT
Filed Feb. 24, 1964
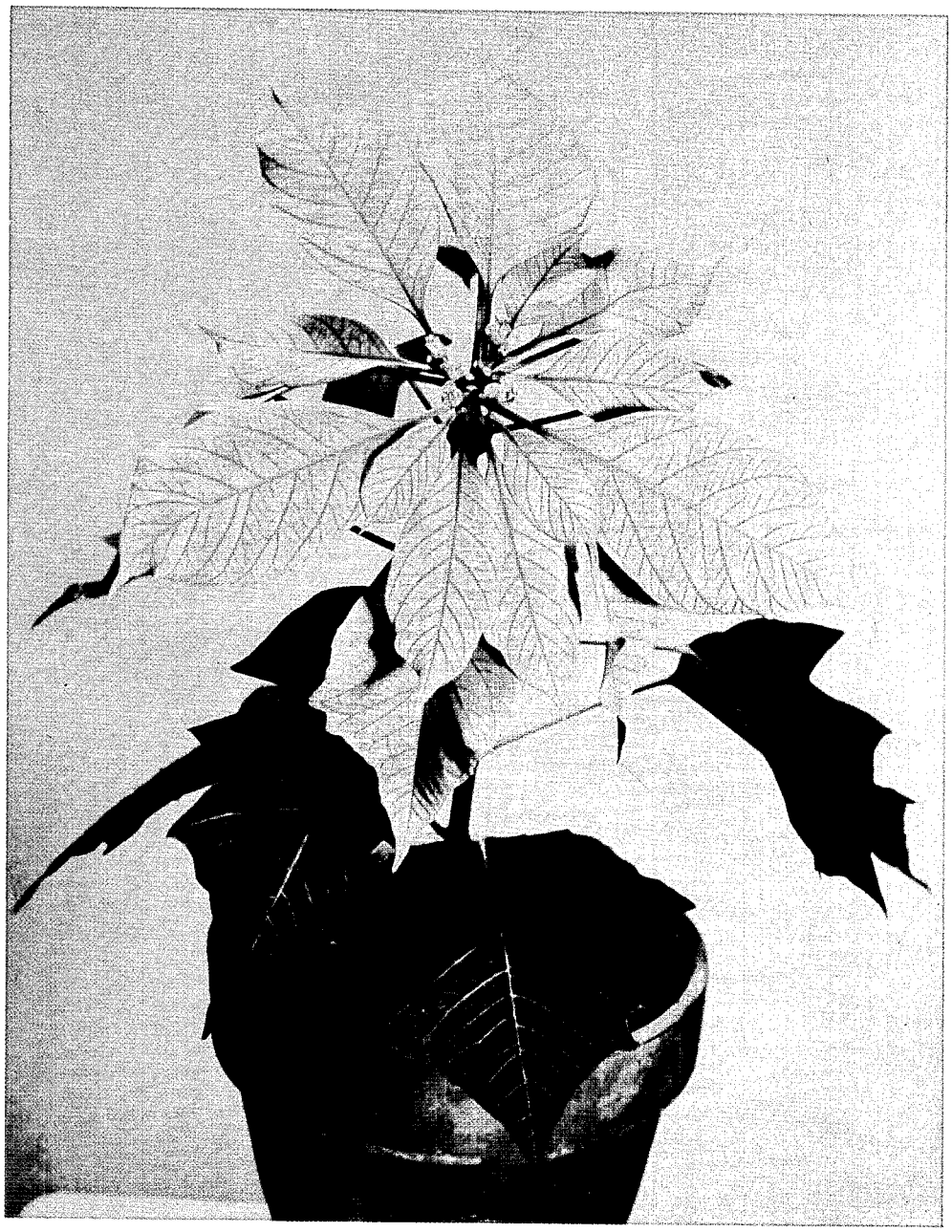
Inventor.
George Y. Kawachi
By: Robb & Robb
Attorneys United States Patent Office Plant Pat. 2,501
Patented Apr. 27, 1965

2,501
POINSETTIA PLANT

George Y. Kawachi, Seattle, Wash., assignor to James C. Mikkelsen, Ashtabula, Ohio Filed Feb. 24, 1964, Ser. No. 347,080
1 Claim. (Cl. Plt.—86)

The present invention relates to a new and distinct variety of poinsettia plant (botanically known as *Euphorbia pulcherrima*), which was discovered by me as a sport of the variety named "Paul Mikkelsen" (Plant Patent No. 2,328).

At the time of my discovery of this new variety, I was growing in my greenhouses at Seattle, Washington, a large block of plants of the parent variety "Paul Mikkelsen." From this block of plants, cuttings were taken by me for producing additional plants therefrom, and from these reproductions, I found several plants which bore pink-colored bracts instead of the characteristic red bracts of the parent variety "Paul Mikkelsen." I thereupon carefully traced the source of these unusual plants and found amongst the original block one particular plant which bore pink bracts on its axillary shoots. The number of cuttings which had been taken from this particular plant corresponded to the number of plants having pink bracts that I had found, which fully confirmed that the new variety had originated as a sport and was capable of being asexually reproduced by cuttings to give the same characteristics as the original sport.

Continued observations of the new poinsettia variety showed that it is endowed with a unique combination of characteristics which are outstanding therein and which distinguish it from its parent, as well as from all other varieties of which I am aware, as follows:

(1) A semi-dwarf habit of growth, combined with rigid stems which do not require staking and which are ideal for short, compact and longer lasting plants for use in home decoration;

(2) A distinctive, attractive and deeper and more uniform pink coloration of the bracts, making the new variety especially desirable for decorative purposes;

(3) Smaller flower buds which do not drop excessive pollen or nectar;

(4) Absence of a tendency of the colored bracts to droop with old age;

(5) Excellent keeping qualities and requiring no exacting growing techniques to prevent early flowering; and (6) Good shipping qualities attributable to the semi-dwarf habits, rigid stems, short leaves and bracts which are less likely to be damaged or injured than in present day commercial varieties.

Like its parent variety "Paul Mikkelsen," the new variety which is the subject hereof is distinctly different from the leading commercial pink variety of poinsettia known as "New Eckes Pink" (unpatented). In this connection, my new variety is more rigid and upright, and therefore not as wild or limp as "New Eckes Pink"; the new variety has shorter and broader leaves, and the bracts are more uniformly colored in a deeper shade of pink without graduations of pink to white or green as in "New Eckes Pink." Thus, in the case of my new variety, the over all color effect is more attractive, which is further accentuated by a more pronounced leaf veining than that of either the parent variety or "New Eckes Pink." The bracts of the new variety are also shorter and wider than those of "New Eckes Pink," but are equally numerous, more rigid and more permanent, and both the foliage and the bracts are maintained on the plant longer, even under severe conditions. Generally, there is less nectar and pollen on the flowers of my new variety than is the case in "New Eckes Pink," and the new variety ships and handles better than that variety.

Asexual reproduction of my new variety by vegatative cuttings propagated under mist at Seattle, Washington, shows that the foregoing characteristics and distinctions come true to form and are established and transmitted through succeeding propagations.

The accompanying drawing shows a typical specimen plant of my new variety as depicted in color as nearly true as it is reasonably possible to make the same in a color illustration of this character.

The following is a detailed description of my new poinsettia variety, with color terminology in accordance with Wilson's Horticultural Colour Chart, except where general color terms of ordinary dictionary significance are obvious, as based on specimens grown at Seattle, Washington, under regular commercial practices:

Parentage: Sport of "Paul Mikkelsen."

Form: Semi-dwarf; compact; upright; no branching.

Habit of growth: Slower than present commercial varieties; no self-branching.

Rooting habit: Substantially identical to that of parent variety "Paul Mikkelsen"; roots are quite fibrous and are less susceptible to root rot organisms than present commercial varieties, as determined by comparison with other varieties grown under comparable conditions at Seattle, Washington.

Blooming habit: Normal.

Blooming season: Late November and December; very suitable for forcing.

Foliage: Alternate on stems; borne on stems at a slight upward angle ranging from about 15° to 20°; foliage does not tend to fall off as the plant matures.

*Size.*—Medium (from about 4 inches to 6 inches long).

*Quantity.*—Above normal.

*Shape.*—Oval pointed (short and stubby pointed).

*Texture.*—Upper side—becomes semi-glossy at maturity; veins have definite recessed and dendritic pattern. Under side—dull; veins have definite protrusion.

*Margin.*—Clean-cut and distinct.

*Color.*—New foliage: upper side—when about ½ inch to ¾ inch long, color is Sap Green, Plate 62, page 62, which changes when leaf is about 2 to 3 inches long to Pod Green, Plate 061, page 120; under side—Pod Green, Plate 061/1, page 120. Old foliage: upper side—Spinach Green, Plate 0960, page 187; under side—Spinach Green, Plate 0960/2, page 187.

Disease resistance: Resistant to botrytis and mildew, as determined by comparison with other plants grown under the same cultural conditions at Seattle, Washington, and which were infected with these diseases.

Bracts: Become more long pointed as flowers develop; bract development continues over a much longer period of time than in other pink poinsettia varieties, and the bracts retain a horizontal position for many months; color holds well for several months; bracts have a slight twisting at the very tip end; leaf veining is quite distinct and draker than the bracts corresponding to that of Claret Rose, Plate 021/1, page 109. Color: upper side—Camellia Rose, Plate 622/1, page 148; under side—Empire Rose, Plate 0621/1, page 183.

Flowers:

*Borne.*—Continuously for several months, with many flowers to a stem in regular clusters in varying stages of development; stems are short and strong.

*Quantity of bloom.*—Relatively abundant; continuous during one season of 3 to 4 months.

*Buds.*—Small; borne on light green stems corresponding in color to that of the buds; flowers drop off gradually after maturity, but new ones continue to develop as the flower stems continue to grow. Color—Scheeles Green, Plate 860/1, page 175.

Reproductive organs:

*Stamens.*—Quite numerous; from ⅛ inch to ¼ inch long. Color—same as bracts in early stages (Camellia Rose, Plate 622/1, page 148), but turning to Currant Red, Plate 821/2, page 167 when the stamens drop.

*Pollen.*—Color—Canary Yellow, Plate 2, page 2.

*Styles.*—Color—Blood Red, Plate 820, page 166.

*Ovaries.*—Color—Scheeles Green, Plate 860/1, page 175.

*Nectar cups.*—Color—Lemon Yellow, Plate 4/1, page 4.

I claim:

A new and distinct variety of poinsettia plant, substantially as herein shown and described, characterized particularly as to novelty by the unique combination of a semi-dwarf habit of growth which produces rigid stems that do not require staking and are ideal for short, compact and long-lasting plants for use in home decorations, a distinctive, attractive, relatively deep and uniform pink color of the bracts, small flowers which are free of excessive pollen or nectar, absence of drooping of the bracts with old age, excellent keeping qualities without requiring exacting growing techniques to prevent early flowering, and good shipping qualities.

No references cited.

ABRAHAM G. STONE, *Primary Examiner.*